United States Patent
Birudukota et al.

(10) Patent No.: US 10,214,496 B2
(45) Date of Patent: Feb. 26, 2019

(54) AZASTEROIDAL MIMICS

(71) Applicants: Nagaraju Birudukota, Miami, FL (US); David Becker, Parkland, FL (US)

(72) Inventors: Nagaraju Birudukota, Miami, FL (US); David Becker, Parkland, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/833,494

(22) Filed: Dec. 6, 2017

(65) Prior Publication Data
US 2018/0155299 A1 Jun. 7, 2018

Related U.S. Application Data

(60) Provisional application No. 62/529,027, filed on Jul. 6, 2017, provisional application No. 62/430,632, filed on Dec. 6, 2016.

(51) Int. Cl.

| | |
|---|---|
| *C07D 255/02* | (2006.01) |
| *C07D 403/14* | (2006.01) |
| *C07D 487/04* | (2006.01) |
| *C07B 43/04* | (2006.01) |
| *C07C 251/20* | (2006.01) |
| *C07C 49/675* | (2006.01) |
| *C07B 45/02* | (2006.01) |
| *C07C 321/06* | (2006.01) |
| *A61P 5/26* | (2006.01) |

(52) U.S. Cl.
CPC ............ *C07D 255/02* (2013.01); *C07B 43/04* (2013.01); *C07B 45/02* (2013.01); *C07C 49/675* (2013.01); *C07C 251/20* (2013.01); *C07C 321/06* (2013.01); *C07D 403/14* (2013.01); *C07D 487/04* (2013.01); *A61P 5/26* (2018.01); *C07C 2603/06* (2017.05)

(58) Field of Classification Search
None
See application file for complete search history.

(56) References Cited

PUBLICATIONS

Becker, David A. Oxocycloalkenyl isoxazolium anhydrobases: synthesis and reactivity studies. Synlett (11), 1993, 866-868.*
Chamberlin, J.W. et al., Structure of Antibiotic A25822 B, A Novel Nitrogen-Containing $C_{28}$-Sterol With Antifungal Properties, *J Antibiot (Tokyo)* 1974, pp. 992-993, vol. 27, No. 12.
Magnus, P. et al., "Mild Regiospecific Rearrangement of α,β-Unsaturated Ketones into Ring Expanded Annulated Tetrazoles," *J. Chem. Soc. Perkin Trans 1*, 1991, pp. 2657-2659.
Micetich, R.G., "Lithiation of five-membered heteroaromatic compounds. The methyl substituted 1,2-azoles, oxadiazoles, and thiadiazoles," *Can. J. Chem.*, 1970, pp. 2006-2015, vol. 48, No. 13.
Rizzo, C.J. et al., Aphidicolin Synthetic Studies: A Stereocontrolled End Game, *J. Chem. Soc. Perkin Trans 1*, 1991, pp. 969-979.

* cited by examiner

*Primary Examiner* — Samantha L Shterengarts
(74) *Attorney, Agent, or Firm* — Saliwanchik, Lloyd & Eisenschenk

(57) ABSTRACT

An azasteroid mimic or an intermediate for the preparation of an azasteroid and azasteroid mimic is formed via an oxocycloalkenyl isoxazolium anhydrobase and its dimer. The dimer can be used to form mono- and dihydrazones, which can be an azasteroid mimic or an intermediate for the preparation of an azasteroid and azasteroid mimic. A method of preparation of the dimer and the azasteroid mimic or an intermediate for the preparation of an azasteroid and azasteroid mimic occurs with hydrazonation and, optionally, a subsequent dehydrazonation. The dimer can be converted by inserting a nitrogen atom into the six membered ring of to a C-17 position cyclohexenone moiety of the dimer to yield a reduced tetrazolo[1,5-a]azepin-8-yl group. A subsequent hydrozone formation at a benzylic ketone can be carried out to generate an azasteroid mimic with a (triazol-4-yl)imino substituent. Monohydrazones can be converted to their thione equivalents.

14 Claims, No Drawings

AZASTEROIDAL MIMICS

CROSS-REFERENCE TO RELATED APPLICATIONS

This application claims the benefit of U.S. Provisional Application Ser. No. 62/529,027, filed Jul. 6, 2017, and U.S. Provisional Application Ser. No. 62/430,632, filed Dec. 6, 2016, the disclosures of which are hereby incorporated by reference in their entireties, including all figures, tables and drawings.

BACKGROUND OF INVENTION

Azasteroids are steroid mimics, a class of natural or synthetic compounds, containing nitrogen in a cyclopentenophenanthrene steroidal nucleus. The replacement of one or more carbon atoms of a steroidal molecule with a heteroatom affects chemical properties and can produce useful alterations in its biological activities. Heterosteroids, and specifically azasteroids, have received much attention among structurally modified natural steroids because of their wide variety of biological activities, often free from undesirable or harmful side effects. One could divide azasteroids into two categories, nuclear and exonuclear, based on the position of heteroatoms. The compounds in which replacement of carbon atoms in the steroidal skeleton at positons 1-17 are nuclear, whereas, when in the side chain or in extra rings the compounds are exonuclear. Nuclear azasteroids are further classified by the position (1-17) of heteroatom or by the ring (A-D) of the steroidal skeleton. For example, the drugs Finasteride and Dutasteride (Avodart) are synthetic, A-ring 4-azasteroids used as 5α-reductase inhibitors. The series of A25822 (A, B, D, L, M, N), natural, homo-D-ring 15-azasteroids was isolated from the mold Geotriclzum flavor-brunneum in 1975. (Chamberlin et al., *J Antibiot* (Tokyo) 1974, 27 (12), 992-3)

In order to find new steroidal molecules with desirable biological effects, natural steroids are often modified at several positions, especially in the cyclopentenophenanthrene ring system with heteroatoms or rings. Replacement of one or more atoms in steroids with heteroatoms (nitrogen) generates new molecules called azasteroids with such diverse biological properties as cytotoxicity, anti-atherogenicity, anti-carcinogenicity, antifungal, antilipemic, local anesthetic, neuromuscular blocking activity, inhibition of steroidal reductases, and more. Certain azasteroid pills are well known contraceptive drugs, due to their binding with steroid receptors, thereby blocking the binding of the actual steroids. Enzymes that normally transform steroids may bind with substrates and form undesirable steroids. Certain azasteroids have an ability to block the biosynthesis of physiologically undesirable steroids.

Selective androgen receptor modulators (SARMs) (non-steroidal) are a novel class of therapeutic compounds having properties similar to anabolic-androgenic steroids (AAS) but more selective in their action. Such selectivity includes androgen receptor specificity, tissue selectivity, fewer steroid-related side effects and, most importantly, an ability to differentiate between anabolic and androgenic activities. These exceptional properties make SARMs unique in the treatment of androgen related complications although they do have the potential for misusage as performance enhancement drugs in sports due to their anabolic properties and an ability to stimulate androgen receptors.

In the process of finding new SARMs, several azasteroidal androgen receptor agonists were designed and synthesized from dihydrotestosterone (DHT). The new azasteroidal selective androgen receptor modulators showed potent human androgen receptor (hAR) binding and low virilizing. Some are useful for the enhancement of weakened muscle tone and amelioration of complications generated by androgen deficiency such as osteoporosis, atherosclerosis, obesity, benign prostatic hyperplasia (BPH), prostate cancer, etc.

Heterosteroids, particularly azasteroids, present challenges in their synthesis, which have prompted synthetic chemists to initiate studies in the total or partial synthesis of these compounds. Most of the synthetic approaches performed on azasteroids followed ring contraction and expansion strategies by using oxidative cleavages or Beckmann rearrangements. The direct synthetic methods leading to the azasteroids are very limited. Intramolecular Diels-alder and cyclization strategies are used in the synthesis of azasteroids as they form cyclic ring structures of the steroidal backbone. Electrocylization involving Stille and Heck coupling as key steps have been used to synthesize azasteroidal compounds.

The design various novel azasteroids with concise synthetic routes to such compounds is desired. The challenges in the synthesis of azasteroids, and the potential of azasteroids as novel drugs have prompted numerous investigations in this field. The synthetic methods leading to steroidal derivatives (azasteroids) with one or more nitrogen atoms are very limited. Generally, oxidative cleavage of the steroidal rings is needed to introduce nitrogen atom(s) in order to synthesize azasteroids. Even though several azasteroidal syntheses have been reported, there is still a need for the development of new methodologies as the previous synthetic methods are limited to particular steroidal structures. Anhydrobases, a class of heterocyclic compounds, are known for their extreme instability. Becker et al., *Synlett* 1993, (11), 866-8 discloses the synthesis and chemistry of anhydrobases in the isoxazole series because of their weak nitrogen-oxygen bond.

Additionally, an azasteroid mimic with heterocyclic ring substitution at the C-17 position may have biological properties similar to VT-1161, a novel oral agent synthesized by Viamet pharmaceutical company, developed for the treatment of onychomycosis, a very common fungal infection of the nail. VT-1161 is a tetrazole derivative and Viamet has other tetrazoles in development.

Prostate cancer is second most common type of cancer and fifth leading cause of cancer related deaths in men. Abiraterone, a steroidal anti-androgen, is a successful drug that is used in the treatment of prostate cancer. Currently, the FDA has approved only one CYP17A1 inhibitor, Abiraterone, which contains a steroidal scaffold that is similar to the endogenous CYP17A1 substrates. It binds in the active site of the enzyme and coordinates the heme iron through its pyridine nitrogen, mimicking the substrate. Galeterone, developed by Tokai pharmaceutical company, has been in phase III clinical trials for castration-resistant prostate cancer. This company announced the discontinuation of its clinical trials on Jul. 26, 2016, after a data of the trial was unlikely to meet its endpoint. Cytochrome P17A1 (CYP17A1) is an enzyme catalyzing biological reactions involved in drug metabolism, synthesis of steroids and other lipids in humans. CYP17A1 is responsible for the production of androgens that are required for the tumor cell growth and became an important target in the treatment of prostate cancer. It possesses an active site that associates with a heme prosthetic group to catalyze biosynthetic reactions. Abiraterone contains a steroidal scaffold that is similar to the endogenous CYP17A1 substrates.

To this end, preparation of novel azasteroidal compounds via an intermediate anhydrobase to a steroidal skeleton and the modification of substituents on the steroidal skeletons might provide congeners with useful biological properties.

BRIEF SUMMARY

An embodiment of the invention is directed to an azasteroid mimic or intermediate for the preparation of an azasteroid mimic consists of an oxocycloalkenyl isoxazolium anhydrobase or an acceptable salt thereof, for example, but not limited to a halide, phosphate, sulfate, or acetate, of the structure:

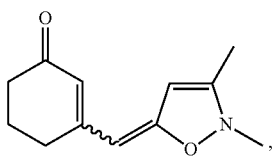

or its dimer or modified dimer of the structure:

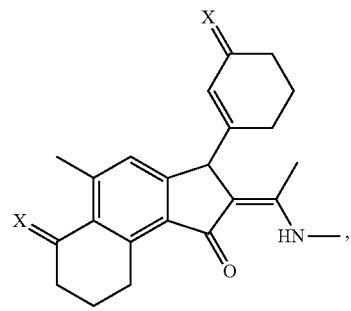

where independently, X=O,

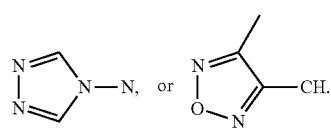

The dimer has the structure:

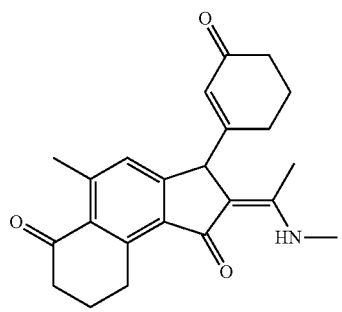 [SMILES: CN/C(C)=C1\C(=O)c2c(cc(C)c3c2CCCC3=O)C1C1=CC(=O)CCC1]

and the azasteroid mimic can be a monohydrazone of the structure:

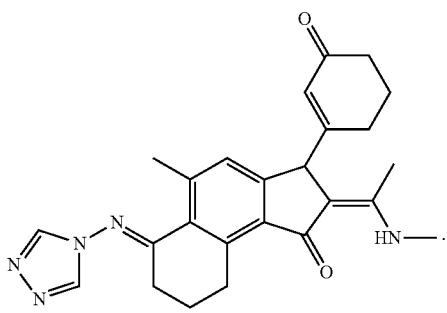 [SMILES: CN/C(C)=C1\C(=O)c2c(cc(C)c3c2CCC/C3=N\n2cnnc2)C1C1=CC(=O)CCC1]

The modified dimer can be a monohydrazone of the structure:

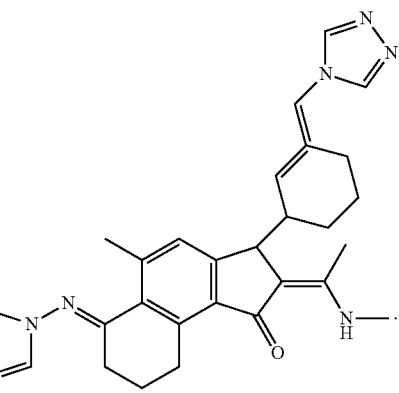

or a dihydrazone of the structure:

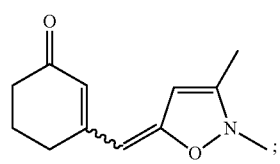

Another embodiment of the invention is directed to a method of preparing the azasteroid mimic or intermediate for the preparation of an azasteroid or azasteroid mimic, where an oxocycloalkenyl isoxazolium anhydrobase of the structure:

is dimerized to a dimer of the structure:

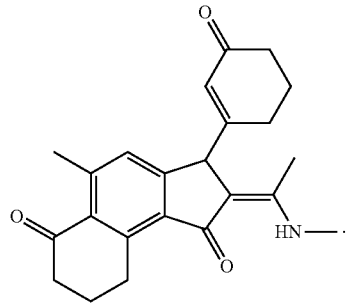 [SMILES: CN/C(C)=C1\C(=O)c2c(cc(C)c3c2CCCC3=O)C1C1=CC(=O)CCC1]

The dimer reacts with one or two equivalents of 4-amino-4H-1,2,4-tirazole to a first monohydrazone, a dihydrazone, or mixture thereof. The reaction can be carried out in the presence of a ketone activating catalyst. The dehydrazonation of the dihydrazone allows the formation of a second monohydrazone other than the first monohydrazone. The azasteroid mimic or intermediate for the preparation of an azasteroid or azasteroid mimic can be isolated by chromatography or other methods.

In another embodiment of the invention an azasteroid mimic or intermediate for its production has the structure:

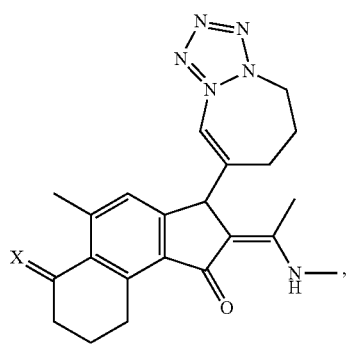

wherein X is O or

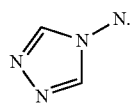

In an embodiment of the invention, the azasteroid mimic can be prepared from a benz[e]indene derivative of the structure:

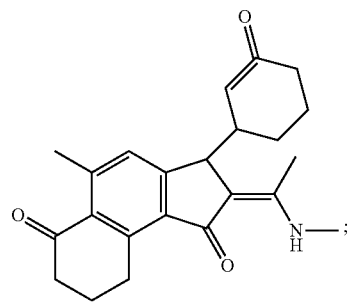

selectively ring-expanding the cycloheneyl ketone with trimethylsilyl azide and trimethylsilyl triflates to form:

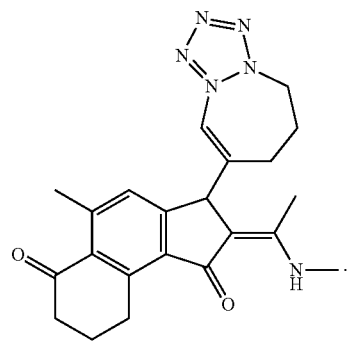

The tetrazolo[1,5-a]azepin-8-yl compound can be further modified by adding 4-amino-4H-1,2,4-tirazole to form:

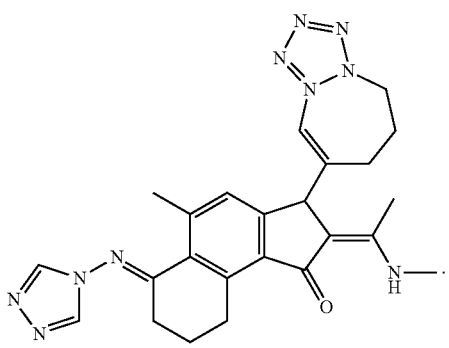

The monohydrazones can be transformed into thiones of the structures:

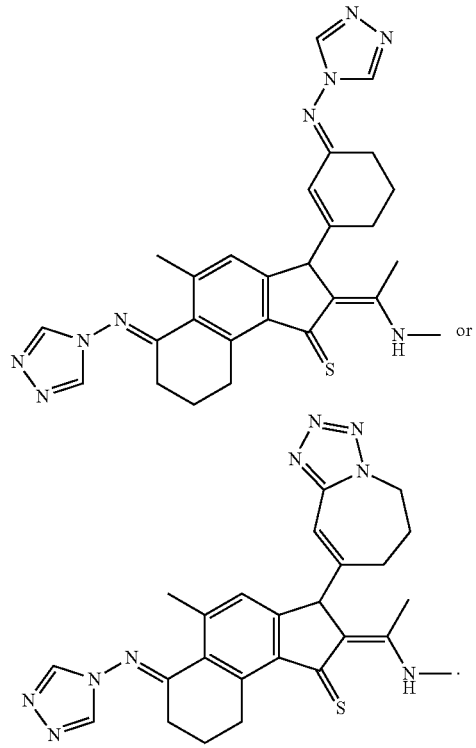

DETAILED DISCLOSURE

Embodiments of the invention are directed to the preparation of an intermediate benz[e]indenedione 46 and the preparation of novel azasteroids and azasteroid mimics therefrom. A facile process starts with commercially available starting materials, for example, but not limited to, 3,5-dimethylisoxazole 42 and carbocyclic vinylogous ester 43, to yield an enone product 44 which is subsequently converted into the corresponding oxocycloalkenyl isoxazolium anhydrobase 45, as indicated in Scheme 1, below.

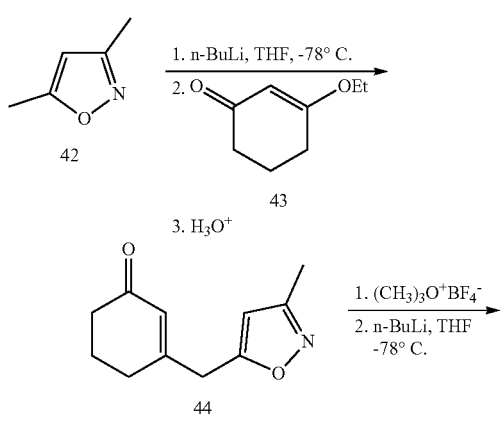

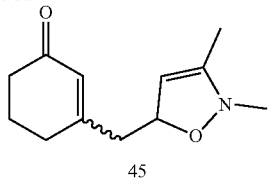

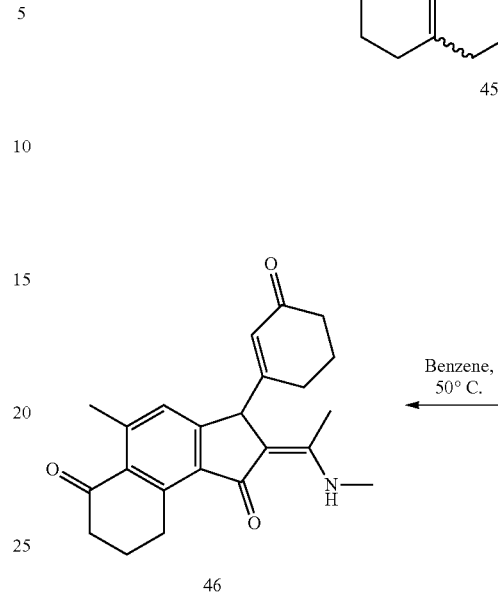

In this example, the lithiation of 3,5-dimethylisoxazole 42 with n-BuLi in THF at −78° C. was performed according to Micetich., *Can. J. Chem.* 1970, 48 (13), 2006-15. The lithiated intermediate participates in a nucleophilic reaction by addition of 3-ethoxy-2-cyclohexen-1-one 43. After acidification of the reaction mixture with 2N HCl, the corresponding enone 44 is obtained in good yield. N-alkylation of enone 44 with trimethyloxonium tetrafluoroborate followed by deprotonation with addition of a solution of n-BuLi in THF at −78° C. afforded the desired anhydrobase 45, where either geometric isomer or a mixture of both can be formed. The new tricyclic benz[e]indenedione 46, a compound produced via initial dimerization of the anhydrobase, was formed when warming 45 in benzene at 50° C. The compound is formed as a pair of enantiomers, which can be separated by chiral chromatography or by formation of diastereomers with a chiral reagent, for example, formation of ammonium salts of a chiral acid, and crystallization.

The dimer 46 provides a platform to establish a six membered A-ring (or a mimic there of) of a steroidal skeleton. Moreover, a dimer such as 46 contains interesting functionality at C-17 along with never before explored vinylogous amide functionality at C-15 and C-16. Specifically, the dimer 46 can be envisioned to afford 1,2-diazasteroid (pyridazinone) 47 and azasteroidal mimic compounds 48 and 49, as shown below. However, the benzylic ketone of 46 is not particularly reactive as the aromatic ring does not provide any additional advantage over other reactive sites on dimer 46 such as the cyclohexenone, the enaminone, and the tertiary benzylic hydrogen present on the five-membered ring.

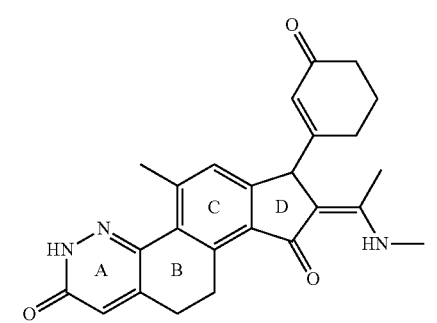

47

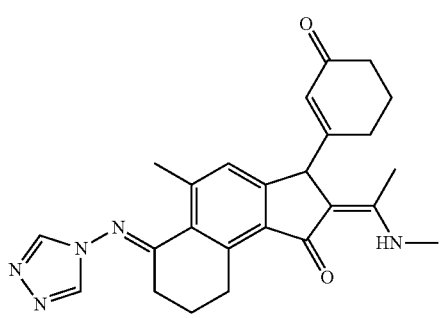

48

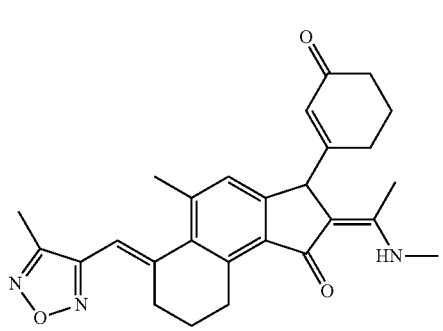

49

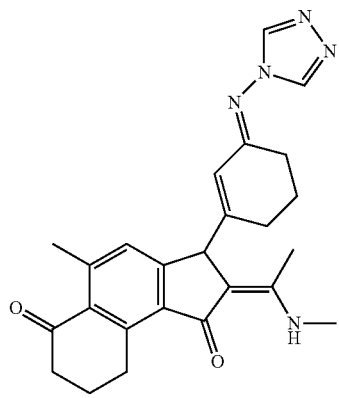

75

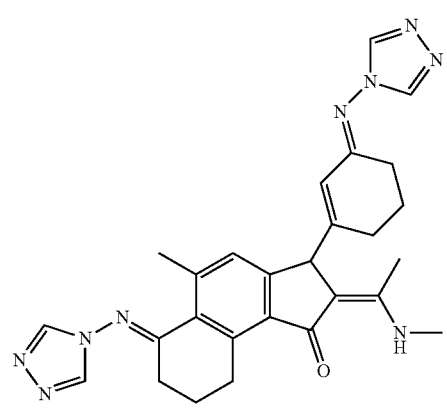

76

To increase the reactivity of the benzylic ketone, the hydrazone formation reaction is carried out in the presence of a ketone activating catalyst, such as, but not limited to, titanium isopropoxide, cerium (III) chloride and scandium triflate. In this manner, triazole reacts with both ketones of dimer 46 to yield about 30% of monohydrazone product (75) (reacting at cyclohexenone carbonyl) and about 30% of bishydrazone product (76), as shown in Scheme 2 below.

Higher yield was afforded by adding the ketone activating catalyst after formation of the kinetically favored 75, which increases the yield bishydrozone 76, as shown in Scheme 3, below.

Scheme 2

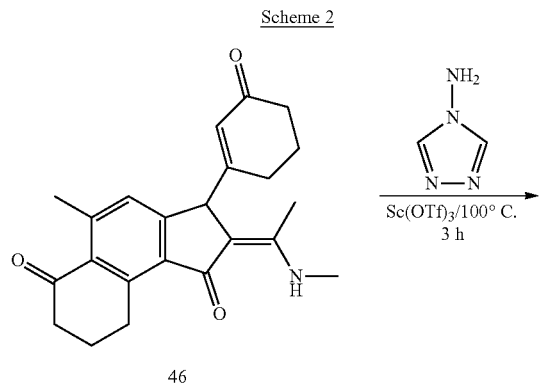

46

Scheme 3

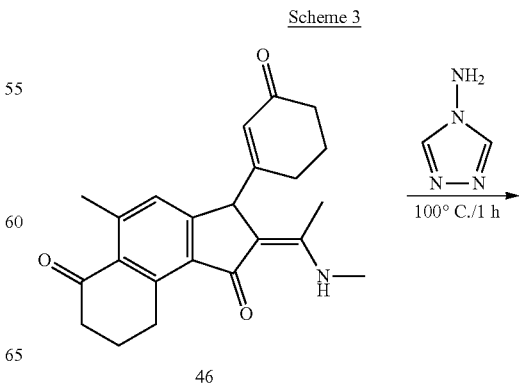

46

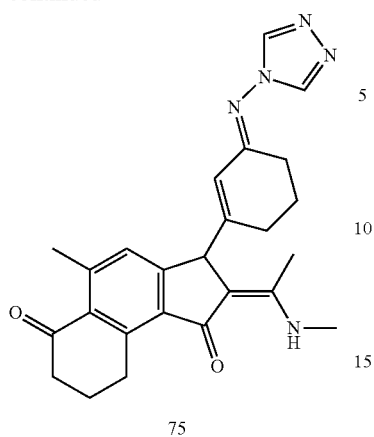

75

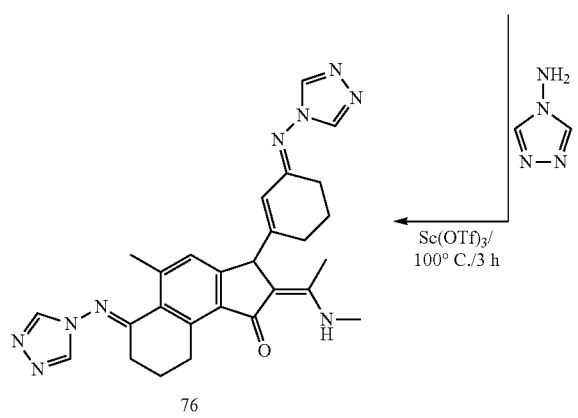

76

In like manner to the hydrozone formation from dimer 46, the dehydrazonation reaction of bishydrozone 76, as shown in Scheme 4, below, allows the selective removal of the hydrozone to afford the desired monohydrozone 48.

Scheme 4

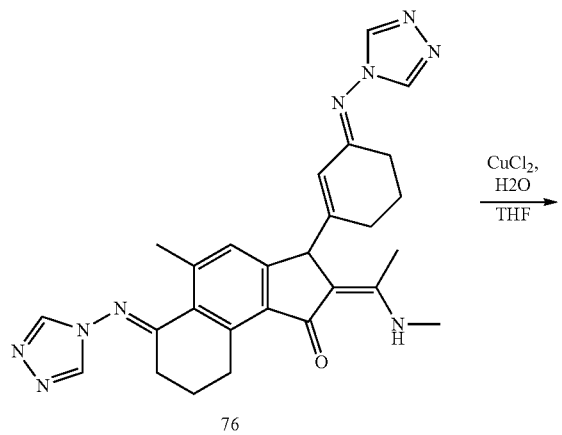

76

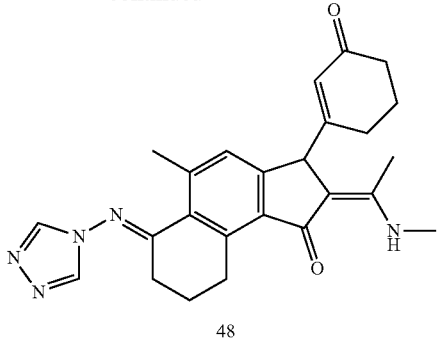

48

All of the compounds above are potential drugs or intermediates in the synthesis for drugs and other biologically active compounds. The reaction intermediates can be modified at any carbon, nitrogen or oxygen in the compounds.

In an embodiment of the invention, regiospecific ring expansion conditions, as taught in Magnus et al. *J. Chem. Soc. Perkin Trans* 1. 1991, 2657-59, is performed on dimer 46, such as treatment of dimer with excess of trimethylsilyl azide and trimethylsilyl triflate, provide compound 80 having a hetero bicyclic ring structure at C-17 position by inserting a nitrogen atom into the six membered ring of cyclohexenone moiety of dimer, as shown in Scheme 5, below. The other benzylic ketone of dimer 46, does not compete, presumably due to the steric influence of a methyl group present on the aromatic ring. This unreacted benzylic ketone undergoes hydrozone formation upon heating with 4-amino-4H-1,2,4-triazole in the presence of a ketone activating catalyst such as scandium triflate, to introduce a triazole ring moiety, which mimics the tetracyclic core of azasteroids, and provides the azasteroidal compound 81.

Scheme 5

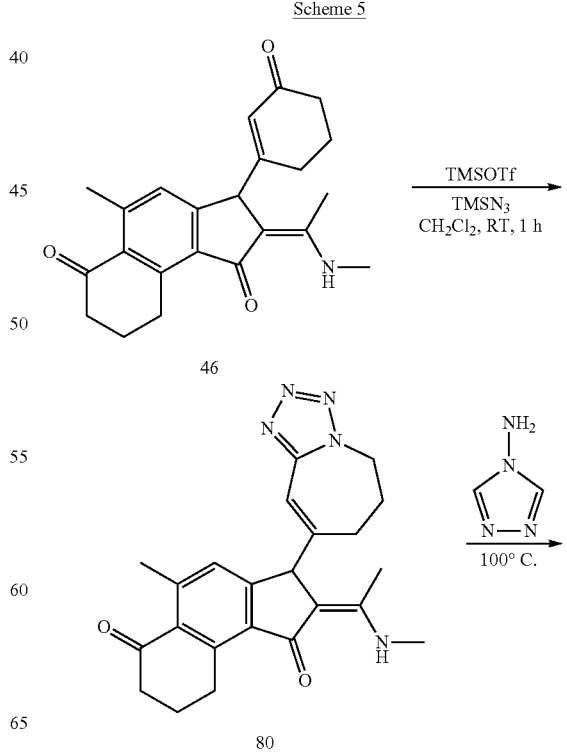

80

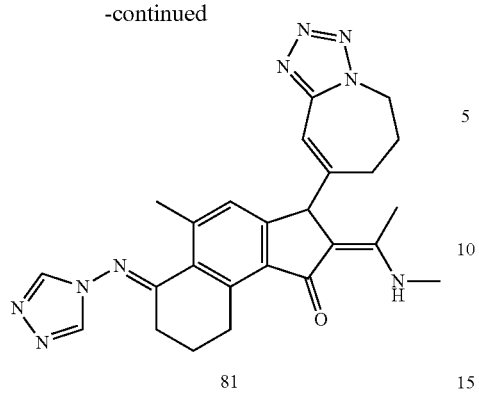

81

Azasteroidal compound 81 has the capacity of binding the active site of the enzyme CYP17A1 similar to Abiraterone, of the structure:

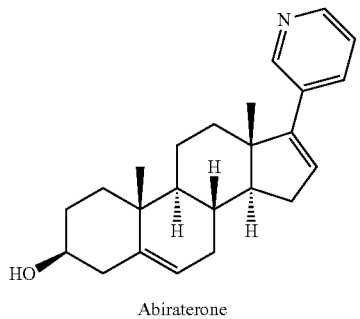

Abiraterone

Compound 81 has the capacity like VT-1161 (a novel oral agent synthesized by Viamet) to treat onychomycosis, a very common fungal infection of the nail. VT-1161, shown below, is a tetrazole derivative. Lanosterol 14α-demethylase (CYP51A1) is an enzyme responsible for the production of ergosterol. This steroid, in animals, alters the rigidity and permeability of plasma membrane of cells. Because ergosterol constitutes a fundamental component of fungal membranes, 14α-demethylase is a target for antifungal agents. Azoles are the most popular and widely used antifungal agents in both agriculture and medicine. These compounds bind as the sixth ligand to the heme group in CYP51, thereby altering the structure of the active site and acting as non-competitive inhibitor.

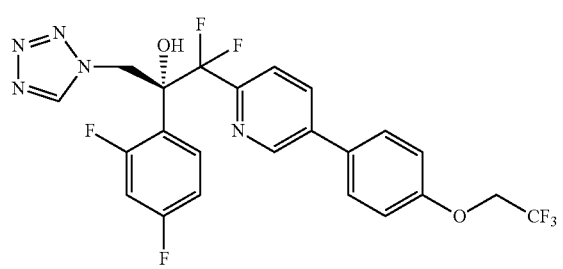

VT-1161

In an embodiment of the invention, as schematically illustrated from compound 81 in scheme 6, the thione compound 82 can be prepared using Lawesson's reagent. In like manner, the thione:

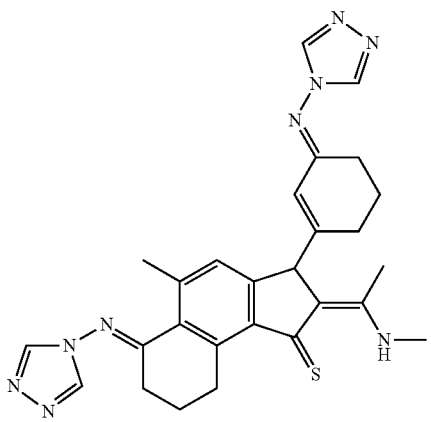

77 can be formed from compound 76.

Scheme 6

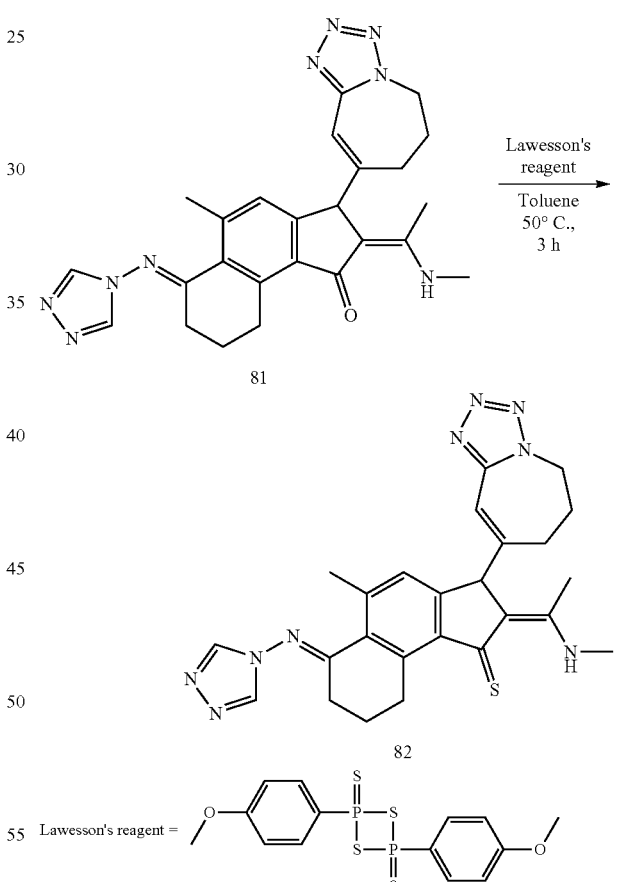

The azasteroidal mimic compounds are potentially biologically active, and have characteristics that suggest activity, as in the compound, abiraterone acetate (Zytiga), which is an antiandrogen used in the management of castration-resistant prostate cancer. The compounds herein can be used as drugs, prodrugs or for other uses. The compounds herein can be formulated in various manners for administration in a variety of ways.

Methods and Materials

3-((3-methylisoxazol-5-yl)methyl)cyclohex-2-ene-1-one (44)

3,5-Dimethylisoxazole 42 (5.0 g, 51.5 mmol) was dissolved in 50 ml dry THF and kept at −78° C. 22.6 ml (1.1 eq) of 2.5 M n-BuLi in hexane was added via cannula to the above mixture over 20 min. After stirring for 30 min, at the same temperature, 3-ethoxycyclohex-2-ene-1-one 43 (7.2 g, 51.5 mmol) was added in one lot with vigorous stirring. The reaction mixture was slowly brought back to the RT, stirred for 30 min and acidified with 35 ml of 2N HCl, which is then extracted with aqueous ammonium chloride and diethyl ether/chloroform. The organic layer was dried, evaporated and purified with silica gel column chromatography by using 4:1 hexane:ethyl acetate starting with pure hexane and slowly increased the polarity with ethyl acetate as eluent. 7.02 g of light orange colored liquid product (71%) was obtained. $^1$H NMR: (400 MHz, CDCl$_3$): δ 5.92 (s, 1H), 5.90 (t, J=1.2 Hz, 1H), 3.62 (s, 2H), 2.38 (t, J=6.8 Hz, 2H), 2.33 (t, J=5.8 Hz, 2H), 2.28 (s, 3H), 2.01 (m, 2H). $^{13}$C NMR: (400 MHz, CDCl$_3$): δ 199.17, 167.88, 160.04, 158.86, 127.88, 103.47, 37.12, 35.04, 29.26, 22.52, 11.39.

3-((2,3-dimethylisoxazol-5(2H)-ylidene)methyl)cyclohex-2-en-1-one (45)

Trimethyloxonium tetrafluoroborate (5.48 g, 36.6 mmol) and 3-((3-methylisoxazol-5-yl)methyl)cyclohex-2-ene-1-one (7.0 g, 36.6 mmol) were added into a two-neck dried flask, which is then stirred under argon until no solid remained. The reaction flask was evacuated, refilled with argon and kept at −78° C. To this reaction mixture, a solution of 16.1 ml of n-BuLi (2.5 M in hexane) in 60 ml of dry THF was added dropwise by using cannula over 30 min period. The reaction flask was slowly brought back to RT over a period of 90 min. A balloon, filled with argon gas, was kept on top of reaction flask's septum to release excess pressure. After stirring 10 min at RT 40 ml of water was added and the resulting solution extracted with chloroform (three times). The organic layers were combined, dried with anhydrous magnesium sulfate and filtered. The solvent was removed under vacuum in dark without heat. The resulting crude compound was purified with silica gel column chromatography by using 9:1 CHCl$_3$:MeOH starting with pure chloroform and slowly increased the polarity with methanol as eluent to yield 7.1 g (74%) of dark yellow colored solid product. $^1$H NMR: (400 MHz, CDCl$_3$): δ 6.15 (s, 1H), 5.43 (s, 1H), 4.82 (s, 1H), 3.23 (s, 3H), 2.47 (t, J=6.0 Hz, 2H), 2.35 (t, J=6.6 Hz, 2H), 2.07 (d, J=0.4 Hz, 3H), 1.97 (m, 2H). $^{13}$C NMR: (400 MHz, CDCl$_3$): δ 198.3, 165.7, 158.7, 155.3, 116.6, 100.7, 88.1, 39.4, 36.6, 30.0, 22.6, 10.9.

5-methyl-2-(1-(methylamino)ethylidene)-3-(3-oxocyclohex-1-en-1-yl)-2,3,8,9-tetrahydro-1H-cyclopenta[a]naphthalene-1,6(7H)-dione (46):

3-((2,3-Dimethylisoxazol-5(2H)-ylidene)methyl)cyclohex-2-en-1-one 45 (5.0 g, 24.3 mmol) was dissolved in 25 ml of anhydrous benzene and heated at 50° C. for 3 hours. The crude solvent was evaporated under vacuum and chromatographed on silica gel with 4:1 hexane:ethyl acetate starting with pure hexane and slowly increased the polarity with ethyl acetate as eluent to get pure red colored solid product (12% yield). $^1$H NMR: (400 MHz, CDCl$_3$): δ 10.90 (d, J=4.8 Hz, 1H), 7.02 (s, 1H), 6.33 (s, 1H), 4.38 (s, 1H), 3.64 (t, J=6.0 Hz, 2H), 3.03 (d, J=5.2 Hz, 3H), 2.69-2.66 (m, 5H), 2.38 (m, 2H), 2.11 (m, 2H) 2.02 (s, 3H), 1.98 (m, 2H), 1.78 (m, 2H). $^{13}$C NMR: (400 MHz, CDCl$_3$): δ 200.10, 199.73, 190.58, 167.05, 161.68, 151.18, 145.12, 144.83, 135.50, 131.69, 128.18, 126.07, 105.62, 50.97, 41.06, 37.80, 29.64, 25.46, 24.37, 24.17, 23.00, 22.59, 15.39. LRMS: (LC/MS, MeOH) m/e 364.19 (MH$^+$).

3-(3-((4H-1,2,4-triazol-4-yl)imino)cyclohex-1-en-1-yl)-5-methyl-2-(1-(methylamino)ethylidene)-2,3,8,9-tetrahydro-1H-cyclopenta[a]naphthalene-1,6(7H)-dione (75)

The dimer compound 46 (0.1 g, 0.27 mmol) was heated with 2 eq of 4-amino-4H-1,2,4-tirazole (46 mg, 0.55 mmol) at 100° C. for 1 h. The reaction was carried out without any solvent. The crude compound was then purified with silica gel column chromatography 9:1 CHCl$_3$:MeOH starting with pure chloroform and slowly increased the polarity with methanol in order to obtain pure product of both isomers in the ratio of 2:1 (83 mg, 71%). $^1$H NMR: (400 MHz, CDCl$_3$): δ 10.90 (m, 1H), 8.27 and 8.22 (s, 2H), 7.06 and 6.86 (s, 1H), 6.68 and 6.35 (s, 1H), 4.47 and 4.27 (s, 1H), 3.64 (m, 21H), 3.04 (d, J=5.6, 3H), 2.69 (m, 5H), 2.44 (m, 2H), 2.07 (s, 3H), 2.12 (m, 2H), 2.01 (m, 2H), 1.78 (m, 2H). $^{13}$C NMR: (400 MHz, CDCl$_3$): δ 200.07, 199.99, 190.52, 190.39, 173.18, 173.08, 166.69, 161.70, 161.57, 161.30, 151.15, 150.57, 145.15, 145.06, 144.95, 144.87, 139.90, 139.70, 135.46, 131.82, 131.68, 125.93, 125.70, 124.06, 123.82, 115.44, 105.44, 105.41, 51.34, 50.97, 41.00, 31.49, 29.61, 27.05, 26.34, 25.42, 24.90, 24.16, 24.01, 22.54, 22.50, 22.19, 21.97, 15.43, 15.32. LRMS: (LC/MS, MeOH) m/e 430.22 (MH$^+$).

6-((4H-1,2,4-triazol-4-yl)imino)-3-(3-((4H-1,2,4-triazol-4-yl)imino)cyclohex-1-en-1-yl)-5-methyl-2-(1-(methylamino)ethylidene)-2,3,6,7,8,9-hexahydro-1H-cyclopenta[a]naphthalen-1-one (76)

The dimer compound 46 (1.0 g, 2.75 mmol) was heated with 4-amino-4H-1,2,4-tirazole (0.92 g, 10.9 mmol) at 100° C. for 3 h in presence of 15 mole percent scandium triflate (0.2 g) as a catalyst. After reaction, the crude compound was chromatographed on silica gel column using 9:1 CHCl$_3$/MeOH starting with pure chloroform and slowly increased the polarity with methanol as an eluent to obtain pure bis-hydrazone compound (0.4 g, 30% yield) along with the monohydrazone compound (0.41 g, 35% yield). $^1$H NMR: (400 MHz, CDCl$_3$): δ 10.93 (m, 1H), 8.24 (t, 4H), 7.17 and 6.97 (s, 1H), 6.70 and 6.36 (s, 1H) 4.50 and 4.29 (s, 1H), 3.63 (m, 3.50 (m, 1H), 3.04 (m, 3H), 2.71 (m, 2H), 2.80 (s, 3H) 2.45 (m, 2H), 2.09 (s, 3H), 1.90 (m, 4H), 1.63 (m, 2H). $^{13}$C NMR: (400 MHz, CDCl$_3$): δ 190.20, 190.07, 175.24, 175.11, 173.10, 166.63, 161.97, 161.61, 150.15, 149.57, 142.88, 142.81, 142.53, 142.42, 139.97, 139.76, 139.61, 135.25, 135.19, 130.29, 130.10, 126.31, 126.04, 123.95, 115.53, 105.52, 51.30, 50.93, 31.53, 29.75, 29.71, 29.28, 27.12, 24.96, 24.84, 24.36, 24.31, 24.04, 22.25, 22.05, 21.46, 15.57, 15.46, 14.15. LRMS: (LC/MS, MeOH) m/e 496.26 (MH$^+$).

6-((4H-1,2,4-triazol-4-yl)imino)-5-methyl-2-(1-(methylamino)ethylidene)-3-(3-oxocyclohex-1-en-1-yl)-2,3,6,7,8,9-hexahydro-1H-cyclopenta[a]naphthalen-1-one (48)

Cupric chloride (27 mg, 0.2 mmol) dissolved in 4 ml of water was added dropwise to the solution of bis-hydrazone compound 76 (0.1 g, 0.2 mmol) dissolved in 3 ml of THF at RT. The reaction process was carefully followed by TLC and the dimer compound started forming after 10 hours of stirring, which indicated that the dehydrozination on tetralone hydrazone moiety started after 10 h of stirring and the reaction was stopped. The crude compound was partitioned between ammonium hydroxide and chloroform. The organic layer was then evaporated and chromatographed on silica gel column using 9:1 $CHCl_3$:MeOH starting with pure chloroform and slowly increasing polarity with methanol as an eluent to obtain pure product (28 mg, 33% in yield). $^1$H NMR: (400 MHz, $CDCl_3$): δ 10.90 (d, J=5.2, 1H), 8.23 (s, 2H), 7.12 (s, 1H), 6.32 (s, 1H), 4.39 (s, 1H), 3.64-3.55 (m, 1H), 3.51-3.43 (m, 1H), 3.03 (d, J=5.2, 3H), 2.70 (t, J=6.8, 2H), 2.65 (s, 3H) 2.36 (m, 2H), 2.02 (s, 3H), 1.95 (m, 2H), 1.82 (m, 2H), 1.61 (m, 2H). $^{13}$C NMR: (400 MHz, $CDCl_3$): δ 199.63, 190.09, 175.22, 166.86, 161.98, 150.09, 142.72, 142.26, 139.53, 135.19, 129.98, 128.13, 126.32, 105.61, 50.81, 37.72, 29.61, 29.19, 24.63, 24.35, 24.27, 22.95, 21.39, 15.36. LRMS: (LC/MS, MeOH) m/e 430.22 ($MH^+$).

(Z)-3-(6,7-dihydro-5H-tetrazolo[1,5-a]azepin-8-yl)-5-methyl-2-(1-(methylamino)ethylidene)-2,3,8,9-tetrahydro-1H-cyclopenta[a]naphthalene-1,6(7H)-dione (80)

To a solution of dimer 46 (50 mg, 1 eq) in 2 ml of anhydrous dichloromethane was added azidotrimethyl silane (47 mg, 3 eq) and trimethylsilyl triflate (92 mg, 3eq) at rt and stirred for 1 h. The reaction progress was carefully followed by TLC and quenched with water when TLC showed no spot of dimer compound. The resulting reaction mixture was extracted with dichloromethane and dried over anhydrous magnesium sulfate. The residue formed on evaporation was purified by silica gel column chromatography with chloroform to obtain pure product 80 (25 mg, 45%) as red colored solid.

$^1$H NMR: (400 MHz, $CDCl_3$): δ 10.90 (d, J=5.2, 1H), 7.12 (s, 1H), 7.07 (s, 1H), 4.55-4.48 (m, 3H), 3.65 (m, 2H), 3.05 (d, J=5.2, 3H), 2.68 (m, 5H), 2.12 (t, J=7.2, 2H), 2.06 (s, 3H), 1.95 (m, 4H).
$^{13}$C NMR: (100 MHz, $CDCl_3$): δ 200.08, 190.64, 161.90, 154.64, 151.38, 151.31, 145.24, 144.90, 135.40, 131.81, 125.97, 111.69, 105.52, 53.16, 49.69, 48.53, 41.04, 40.26, 31.32, 29.64, 28.40, 25.48, 24.14, 22.98, 22.59, 15.63, 15.41.

(2Z,6E)-6-((4H-1,2,4-triazol-4-yl)imino)-3-(6,7-dihydro-5H-tetrazolo[1,5-a]azepin-8-yl)-5-methyl-2-(1-(methylamino)ethylidene)-2,3,6,7,8,9-hexahydro-1H-cyclopenta[a]naphthalen-1-one (81):

A mixture of compound 80 (25 mg, 1 eq) and excess of 4-amino-4H-1,2,4-tirazole (20 mg) was heated at 100° C. for 3 h in the presence of scandium triflate (15 mol %). The resulting reaction residue was purified by silica gel column chromatography with chloroform/methanol (9:1) to obtain corresponding pure hydrazone 81 (8 mg, 30%) as a red solid product.
$^1$H NMR: (400 MHz, $CDCl_3$): δ 10.97 (d, J=5.2, 1H), 8.27 (d, 2H), 7.19 (s, 1H), 7.15 (s, 1H), 4.62-4.51 (m, 3H), 3.65 (m, 2H), 3.05 (d, J=5.2, 3H), 2.61 (m, 5H), 2.11 (t, J=7.2, 2H), 2.08 (s, 3H), 1.92 (m, 4H).
$^{13}$C NMR: (100 MHz, $CDCl_3$): δ 190.24, 175.16, 162.21, 154.52, 151.36, 150.29, 142.92, 142.40, 139.57, 135.15, 130.20, 126.83, 126.28, 111.77, 105.56, 53.10, 49.68, 29.69, 29.27, 28.45, 25.04, 24.90, 24.70, 24.37, 23.00, 21.47, 21.33, 15.46.

HRMS: (LC/MS, MeOH) m/z 470.24 ($MH^+$).

All publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An azasteroid mimic or intermediate for the preparation of an azasteroid and azasteroid mimic, consisting of an oxocycloalkenyl isoxazolium anhydrobase, or any salt thereof, where the oxocycloalkenyl isoxazolium anhydrobase is a modified dimer of

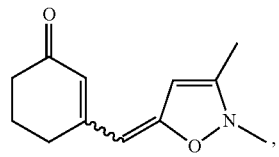

having the structure:

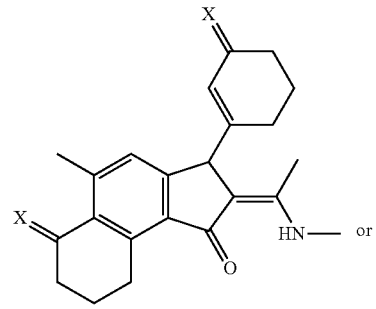

or

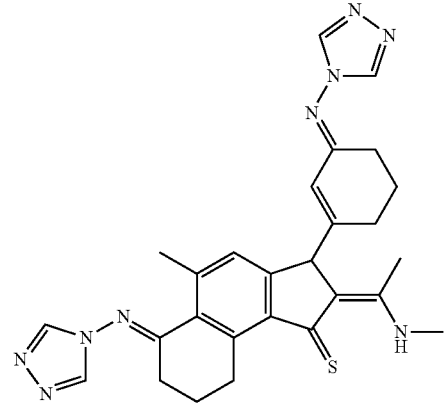

where independently,
X=O,

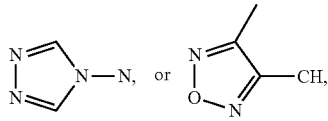

wherein at least one X is not O; or a ring-expanded dimer of the structure:

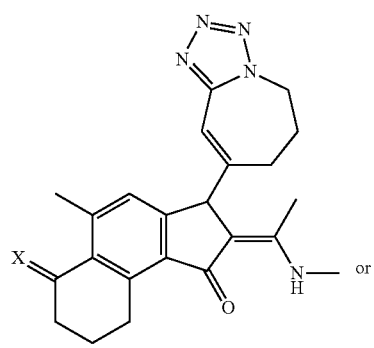

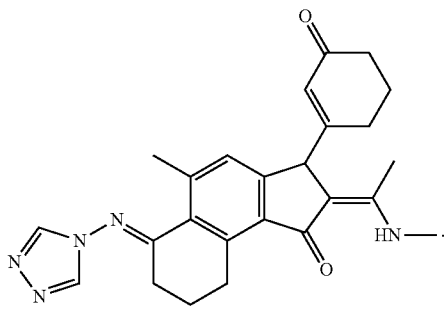 [SMILES: CN/C(C)=C1\C(=O)c2c(cc(C)c3c2CCC/C3=N\n2cnnc2)C1C1=CC(=O)CCC1]

3. The azasteroid mimic or intermediate for the preparation of an azasteroid or azasteroid mimic according to claim 1, wherein the modified dimer is a monohydrazone of the structure:

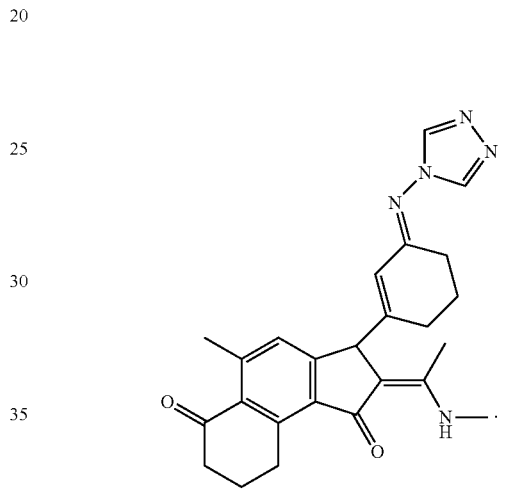

4. The azasteroid mimic or intermediate for the preparation of an azasteroid or azasteroid mimic according to claim 1, wherein the modified dimer is a dihydrazone of the structure:

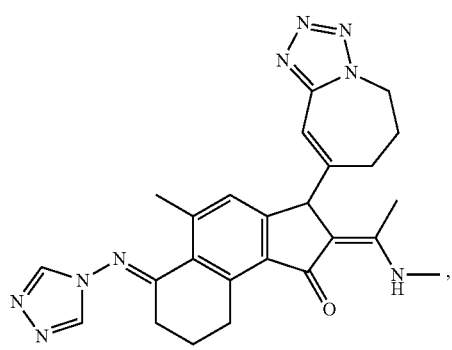

wherein X is O or

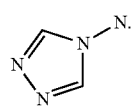

2. The azasteroid mimic or intermediate for the preparation of an azasteroid or azasteroid mimic according to claim 1, wherein the azasteroid mimic is a monohydrazone of the structure:

5. The azasteroid mimic or intermediate for the preparation of an azasteroid and azasteroid mimic, according to claim 1, wherein the structure is:

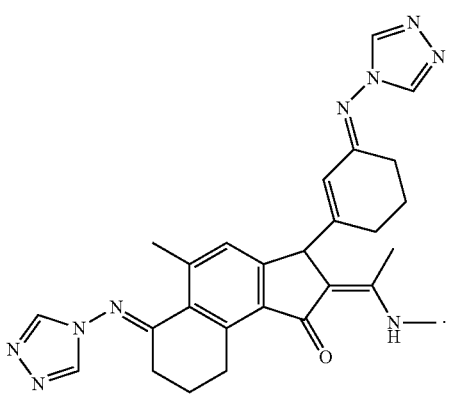 [SMILES: CN/C(C)=C1\C(=O)c2c(cc(C)c3c2CCC/C3=N\n2cnnc2)C1C1=C/C(=N/n2cnnc2)CCC1]

6. The azasteroid mimic or intermediate for the preparation of an azasteroid and azasteroid mimic, according to claim 1, wherein the structure is:

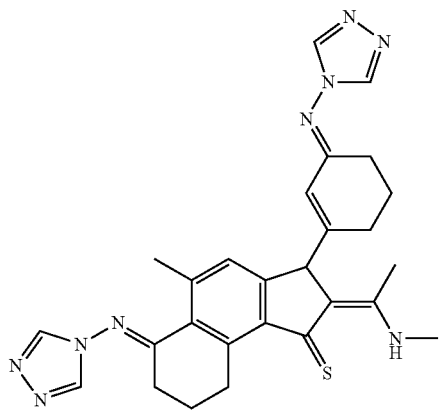 [SMILES: CN/C(C)=C1\C(=S)c2c(cc(C)c3c2CCC/C3=N\n2cnnc2)C1C1=C/C(=N/n2cnnc2)CCC1]

7. The azasteroid mimic or intermediate for the preparation of an azasteroid and azasteroid mimic, according to claim 1, wherein the structure is:

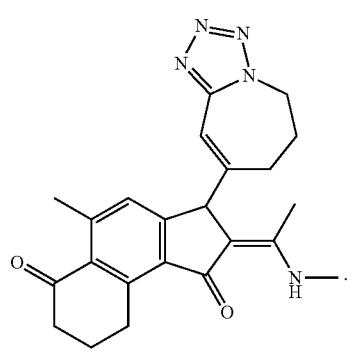

8. The azasteroid mimic or intermediate for the preparation of an azasteroid and azasteroid mimic, according to claim 1, wherein the structure is:

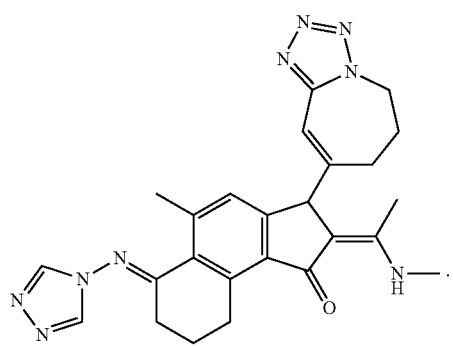 [SMILES: CN/C(C)=C1\C(=O)c2c(cc(C)c3c2CCC/C3=N\n2cnnc2)C1C1=Cc2nnnn2CCC1]

9. A method of preparing an azasteroid mimic or intermediate for the preparation of an azasteroid or azasteroid mimic according to claim 1, comprising:

providing an oxocycloalkenyl isoxazolium anhydrobase of the structure:

dimerizing the oxocycloalkenyl isoxazolium anhydrobase to a dimer of the structure:

optionally, selectively ring-expanding the cycloheneyl ketone with trimethylsilyl azide and trimethylsilyl triflates to form a dimer of the structure:

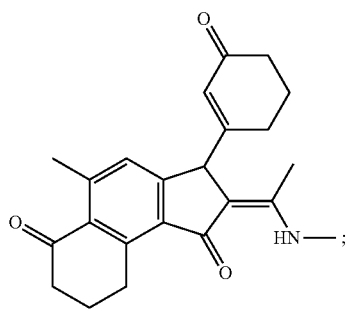 [SMILES: CN/C(C)=C1\C(=O)c2c(cc(C)c3c2CCCC3=O)C1C1=CC(=O)CCC1]

reacting the dimer with one or two equivalents of 4-amino-4H-1,2,4-tirazole to a first monohydrazone, a dihydrazone, or mixture thereof optionally, in the presence of a ketone activating catalyst;

optionally, transforming the ketone of the first monohydrazone to a thione of the structure:

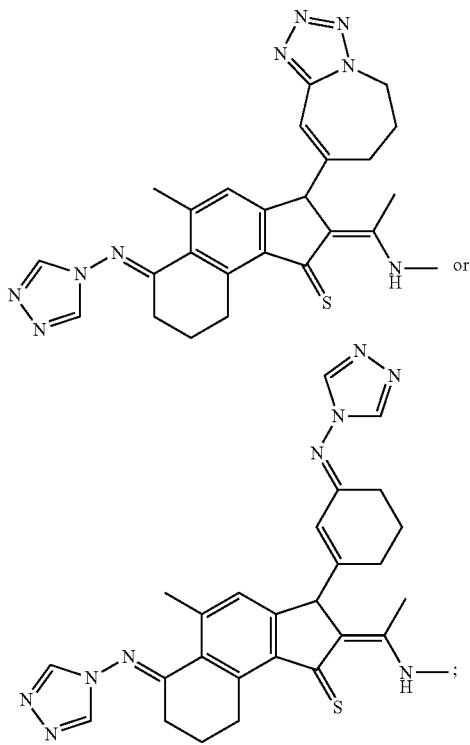

optionally, dehydrazonating the dihydrazone to a second monohydrazone;

and isolating the azasteroid mimic or intermediate for the preparation of an azasteroid or azasteroid mimic.

10. The method of claim 9, wherein the ketone activating catalyst is titanium isopropoxide, cerium (III) chloride or scandium triflates.

11. The method of claim 9, wherein the ketone activating catalyst is scandium triflates.

12. The method of claim 9, wherein the 4-amino-4H-1,2,4-tirazole is added in a first addition and the ketone activating catalyst is added after formation of the monohydrazone to convert at least a portion of the monohydrazone to a dihydrazone.

13. The method of claim 9, wherein the dehydrazonating is catalyzed by cupric chloride.

14. The method of claim 9, wherein the transforming to a thione is reacting with Lawesson's reagent.

* * * * *